(12) United States Patent
Glukhovsky et al.

(10) Patent No.: US 7,650,180 B2
(45) Date of Patent: Jan. 19, 2010

(54) IMAGING SENSOR ARRAY AND DEVICE AND METHOD FOR USE THEREFOR

(75) Inventors: Arkady Glukhovsky, Santa Clarita, CA (US); Shmuel Gan, Qiriat Ata (IL); Israel Mendel, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 109 days.

(21) Appl. No.: 10/562,865

(22) PCT Filed: Jul. 4, 2004
(Under 37 CFR 1.47)

(86) PCT No.: PCT/IL2004/000595

§ 371 (c)(1),
(2), (4) Date: Oct. 4, 2006

(87) PCT Pub. No.: WO2005/004033

PCT Pub. Date: Jan. 13, 2005

(65) Prior Publication Data

US 2007/0078298 A1     Apr. 5, 2007

Related U.S. Application Data

(60) Provisional application No. 60/483,893, filed on Jul. 2, 2003.

(51) Int. Cl.
*A61B 5/05* (2006.01)
(52) U.S. Cl. .................... 600/476; 600/160
(58) Field of Classification Search .......... 600/407, 600/424, 437, 472, 109, 300, 160, 473, 476; 348/76; 604/890.1, 93, 114; 346/33; 455/570, 455/557, 569.2
See application file for complete search history.

(56) References Cited

U.S. PATENT DOCUMENTS

| | | | |
|---|---|---|---|
| 3,322,374 A | 5/1967 | King, Jr. | |
| 4,219,821 A | 8/1980 | Selim | |
| 4,246,792 A | 1/1981 | Matzuk | |
| 4,278,077 A | 7/1981 | Mizumoto | |
| 4,329,881 A | 5/1982 | Schloss | |
| 4,431,005 A | 2/1984 | McCormick | |
| 4,936,823 A | 6/1990 | Colvin et al. | |
| 5,042,486 A | 8/1991 | Pfeiler et al. | |

(Continued)

FOREIGN PATENT DOCUMENTS

EP     0 667 115     8/1995

(Continued)

OTHER PUBLICATIONS

U.S. Appl. No. 10/493,751, filed Apr. 27, 2004, Glukhovsky et al.

(Continued)

*Primary Examiner*—Eric F Winakur
*Assistant Examiner*—Lawrence N Laryea
(74) *Attorney, Agent, or Firm*—Pearl Cohen Zedek Latzer, LLP

(57) ABSTRACT

A system and method for receiving an in vivo signal, using for example a receiver, a recorder and an antenna array. The receiver may include for example a switching unit and an amplifier, and may be in proximity to the antenna array.

7 Claims, 7 Drawing Sheets

U.S. PATENT DOCUMENTS

| | | | |
|---|---|---|---|
| 5,211,165 A | 5/1993 | Dumoulin et al. | |
| 5,217,449 A | 6/1993 | Yuda et al. | |
| 5,279,607 A | 1/1994 | Schentag et al. | |
| 5,429,132 A | 7/1995 | Guy et al. | |
| 5,515,853 A | 5/1996 | Smith et al. | |
| 5,592,180 A | 1/1997 | Yokev et al. | |
| 5,604,531 A * | 2/1997 | Iddan et al. | 348/76 |
| 5,643,175 A | 7/1997 | Adair | |
| 5,681,260 A | 10/1997 | Ueda et al. | |
| 5,697,377 A | 12/1997 | Wittkampf | |
| 5,697,384 A | 12/1997 | Miyawaki et al. | |
| 5,720,293 A | 2/1998 | Quinn et al. | |
| 5,736,958 A | 4/1998 | Turpin | |
| 5,747,996 A | 5/1998 | Fuchs | |
| 5,913,820 A | 6/1999 | Bladen et al. | |
| 5,993,378 A | 11/1999 | Lemelson | |
| 6,172,640 B1 | 1/2001 | Durst et al. | |
| 6,188,355 B1 | 2/2001 | Gilboa | |
| 6,190,395 B1 | 2/2001 | Williams | |
| 6,233,476 B1 | 5/2001 | Strommer et al. | |
| 6,240,312 B1 | 5/2001 | Alfano et al. | |
| 6,254,548 B1 | 7/2001 | Ishikawa et al. | |
| 6,298,255 B1 | 10/2001 | Cordero et al. | |
| 6,304,769 B1 | 10/2001 | Arenson et al. | |
| 6,308,089 B1 | 10/2001 | von der Ruhr et al. | |
| 6,428,469 B1 | 8/2002 | Iddan et al. | |
| 6,453,190 B1 | 9/2002 | Acker et al. | |
| 6,580,938 B1 | 6/2003 | Acker | |
| 6,632,175 B1 | 10/2003 | Marshall | |
| 6,676,600 B1 | 1/2004 | Conero et al. | |
| 6,689,056 B1 | 2/2004 | Kilcoyne et al. | |
| 6,690,963 B2 | 2/2004 | Ben-Haim et al. | |
| 6,709,387 B1 | 3/2004 | Glukhovsky et al. | |
| 6,904,308 B2 | 6/2005 | Frisch et al. | |
| 6,934,573 B1 | 8/2005 | Glukhovsky et al. | |
| 6,951,536 B2 | 10/2005 | Yokoi et al. | |
| 2001/0035902 A1 | 11/2001 | Iddan et al. | |
| 2002/0103417 A1 | 8/2002 | Gazdzinski | |
| 2002/0165592 A1 | 11/2002 | Glukhovsky et al. | |
| 2002/0173718 A1 | 11/2002 | Frisch et al. | |
| 2003/0013370 A1 | 1/2003 | Glukhovsky | |
| 2003/0043263 A1 | 3/2003 | Glukhovsky et al. | |
| 2003/0045790 A1 | 3/2003 | Lewkowicz et al. | |
| 2003/0073935 A1 | 4/2003 | Segawa et al. | |
| 2003/0085994 A1 | 5/2003 | Fujita et al. | |
| 2003/0114742 A1 | 6/2003 | Lewcowicz et al. | |
| 2003/0117491 A1 | 6/2003 | Avni et al. | |
| 2003/0139661 A1 * | 7/2003 | Kimchy et al. | 600/407 |
| 2003/0167000 A1 | 9/2003 | Mullick et al. | |
| 2003/0171653 A1 | 9/2003 | Yokoi et al. | |
| 2003/0208107 A1 | 11/2003 | Refael | |
| 2004/0073087 A1 | 4/2004 | Glukhovsky et al. | |
| 2004/0087832 A1 | 5/2004 | Glukhovsky et al. | |
| 2005/0004473 A1 | 1/2005 | Fujita et al. | |
| 2005/0043634 A1 | 2/2005 | Yokoi et al. | |

FOREIGN PATENT DOCUMENTS

| | | |
|---|---|---|
| EP | 0667115 | 8/1995 |
| EP | 1260176 | 11/2002 |
| JP | 4-144533 | 5/1992 |
| JP | 6-114037 | 4/1994 |
| JP | 6114064 | 4/1994 |
| JP | 6154191 | 6/1994 |
| JP | 6285044 | 10/1994 |
| JP | 1995-111985 | 5/1995 |
| JP | 711985 | 5/1995 |
| JP | 7255692 | 10/1995 |
| JP | 2001-046358 | 2/2001 |
| JP | 2001-231186 | 8/2001 |
| JP | 2001-231187 | 8/2001 |
| JP | 2002000556 | 1/2002 |
| WO | WO 98/11816 | 3/1998 |
| WO | WO 99/32028 | 7/1999 |
| WO | WO 00/10456 | 3/2000 |
| WO | WO 01/06917 | 2/2001 |
| WO | WO 01/08548 | 2/2001 |
| WO | WO 01/65995 | 9/2001 |
| WO | WO 03/011103 | 2/2003 |
| WO | WO 03/021529 | 3/2003 |
| WO | WO 03/028224 | 4/2003 |
| WO | WO 2004/036803 | 4/2004 |
| WO | WO 2004/088448 | 10/2004 |
| WO | WO 2005/004033 | 1/2005 |

OTHER PUBLICATIONS

International Search Report PCT/IL04/00595 Mailed Mar. 23, 2006.
"Localization of a wireless capsule endoscope in the GI Tract", Gastrointestinal Endoscopy 2001;53:AB126.
Nam, et al., "A method for Position Detection of the wireless capsule endoscopes Module Using the Solution of Nonlinear Simultaneous Equations", Sensors Conference 2002, p. 377.
Nam, et al., "A method for Position Detection of Miniaturized Telemetry Module Using the Solution of Nonlinear Simultaneous Equations", 2002.
Park, et al., "A Technique for Position Detection of Miniatured Wireless Telemetry Module in the Human Body", Proceedings of the 32nd ISR (International Symposium on Robotics); Apr. 19-21, 2001,pp. 1888-1892.
Park, et al., "Design of Bi-directional and Multi-Channel Miniaturized Telemetry Module for Wireless Endoscopy", $2^{nd}$ Annual International IEEE-EMBS Special Topic Conference on Microtechnologies in Medicine &Biology, May 2-4, 2002, Madison, Wisconsin USA pp. 273-276.
Park, et al., "Design of Miniaturized Telemetry Module for Bi-Directional Wireless Endoscopy", May 2-4, 2002.
Park, et al., "A Technique for Localization of Biomedical Telemetry Sensor in Human Body", Proceedings of the International Sensor Conference 2001, Seoul, Korea.
PCT Search Report International Application No. PCT/IL02/00386 International Filing Date: May 19, 2002.
Rowell, Nancy D., Endoscopes Go Wireless, Biophotonics in Action, Photonics Spectra, Mar. 2001.
www.ibcdigital.com/ibc/animation_galleries/visualization.
www.rfnorkia.com—NORIKA3, Dec. 24, 2001.
Supplementary European Search Report of Application No. EP 04 74 4935 dated Feb. 11, 1009.

* cited by examiner

IMAGING SENSOR ARRAY AND DEVICE AND METHOD FOR USE THEREFOR

CROSS-REFERENCE TO RELATED APPLICATIONS

This application is a National Phase Application of PCT International Application Number PCT/IL2004/000595, International Filing Date Jul. 4, 2004, entitled "Imaging Sensor Array and Device and Method for Use Thereof", published on Jan. 13, 2005 as International Application Publication Number WO 05/004033, which is incorporated herein by reference in its entirety; which in turn claims priority and benefit from U.S. Provisional Patent Application No. 60/483,893, filed on Jul. 2, 2003, entitled "Imaging Sensor Array and Device and Method for Use Thereof", which is hereby incorporated by reference in its entirety.

FIELD OF THE INVENTION

The present invention relates to a device, system and method of imaging or in-vivo sensing, specifically to a device, system and method using a sensor array receiving and/or recording data captured in-vivo.

BACKGROUND OF THE INVENTION

Devices and methods for performing in-vivo imaging of passages or cavities within a body, and for gathering information other than or in addition to image information (e.g., temperature information, pressure information), are known in the art. Such devices may include, inter alia, various endoscopic imaging systems and devices for performing imaging in various internal body cavities.

An in-vivo imaging device may include, for example, an imaging system for obtaining images from inside a body cavity or lumen, such as the GI tract. The imaging system may include, for example, an imager associated with an optical system, and optionally an illumination unit, a transmitter and/or an antenna. Other types of in-vivo devices exist, such as endoscopes which may not require a wireless transmitter, and devices performing functions other than imaging.

Some in-vivo imaging systems use multiple cables, sensors and/or antennas to receive and/or record signals and/or data transmitted by an imaging device. For example, some in-vivo imaging systems require firm attaching of multiple sensors to a user's skin and/or body; such firm attaching may require gluing or bonding of sensors to a user's skin and/or body. In some imaging systems, multiple cables, sensors and/or antennas are used such that it may result in inefficient operation and/or inconvenient usage.

Therefore there is a need for a system and a method which will improve the noise figure, and will decrease the amount of cables between antenna array and the recorder.

SUMMARY OF THE MENTION

Various embodiments of the invention provide, for example, an imaging system using a sensor array, which may be used, for example, in conjunction with an in-vivo imaging device or other sensing device.

Embodiments of the invention provide, for example, an in-vivo imaging system able to receive and/or record signals, data and/or transmissions, using a sensor array and/or an antenna array.

Embodiments of the invention provide, for example, an in-vivo imaging system able to receive and/or record signals, data and/or transmissions, using a sensor array and/or an antenna array incorporated within a wearable garment and/or article of clothing, for example, a wearable vest or shirt.

Embodiments of the invention provide, for example, an in-vivo imaging system able to receive and/or record signals, data and/or transmissions, using a sensor, sensors, an antenna and/or antennas, which may be attached to a user's skin and/or body by adhesion, either directly and/or indirectly, for example, using an adhesive sleeve.

Embodiments of the invention provide, for example, an in-vivo imaging system able to receive and/or record signals, data and/or transmissions, using a sensor array and/or an antenna array and/or an amplifier and/or a pre-amplifier.

Embodiments of the invention provide, for example, an in-vivo imaging system able to receive and/or record signals, data and/or transmissions, using a sensor array and/or an antenna array and/or a selection switch to select one or more from a plurality of antennas and/or sensors.

Embodiments of the invention provide, for example, an in-vivo imaging system able to receive and/or record signals, data and/or transmissions, using a sensor array and/or an antenna array and/or a single cable and/or a reduced number of cables and/or a reduced number of connectors to connect the array to a recorder.

A sensor array and/or an antenna array in accordance with embodiments of the invention may be used in applications other than an in-vivo imaging system.

BRIEF DESCRIPTION OF TEE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
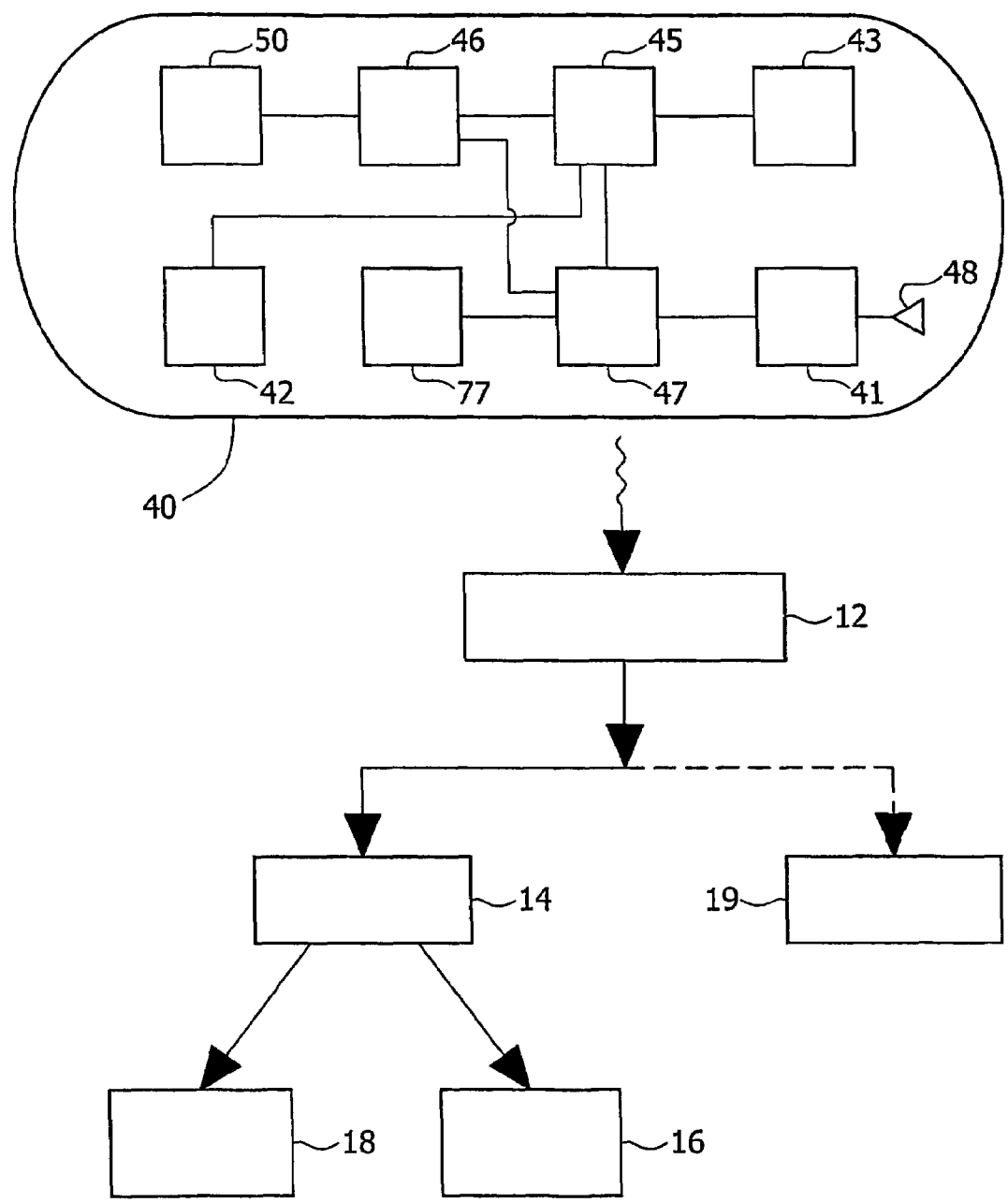
FIG. 1 is a schematic illustration of an in-vivo imaging system in accordance with an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order so as not to obscure the invention.

It is noted that some embodiments of the present invention are directed to a system for use with a typically swallowable in-vivo device. Other embodiments need not be for use with a device that is swallowable. Devices used with embodiments of the present invention may be similar to embodiments described in International Application WO 01/65995 and/or in U.S. Pat. No. 5,604,531, each of which are assigned to the common assignee of the present invention and each of which are hereby fully incorporated by reference. Furthermore, a receiving and/or display system suitable for use with embodiments of the present invention may also be similar to embodiments described in WO 01/65995 and/or in U.S. Pat. No. 5,604,531. Of course, devices and systems as described herein may have other configurations and other sets of components.

Alternate embodiments of the device, system and method according to various embodiments of the invention may be used with other devices, including non-imaging and/or non-in-vivo devices.

In some embodiments, a receiving system may be placed on a patient that may, for example, produce stronger signals, be easier to use, and/or provide other benefits. For example, the receiving system may collect signals at a point that is electrically or physically close to a set of antennas, enabling, for example, amplification or processing. Such amplification or processing may be done in a unit that is closer, electrically, to the antenna or antennas than other units, such as a recorder unit. For example, a set (where set may include one) of antennas may send signals to a recording or other unit, and an amplification or other signal processing unit, which may be separate from both the antennas and recording unit may be placed in an intermediate location. The receiving system may also enable the consolidation of cables or signals, so that if multiple antennas are used, for at least a portion of the signal path may involve only one cable. Of course, other configurations and benefits are possible.

Reference is made to FIG. 1, which shows a schematic diagram of an embodiment of an in-vivo imaging system. In one embodiment, the system may include a device 40 having an imager 46, an illumination source 42, and a transmitter 41. In some embodiments, device 40 may be implemented as a swallowable capsule, but other sorts of devices or suitable implementations may be used. Outside a patient's body may be a device 12, a storage unit 19, a data processor 14, and an image monitor 18. Other systems and methods of storing and/or displaying collected image data may be used. It is noted that in some embodiments, device 12, data processor 14 and/or other components of device 40 and/or of the system of FIG. 1 may be similar to that described in the above-mentioned International Application WO 01/65995 and/or U.S. Pat. No. 5,604,531, with suitable modifications; in alternate embodiments, these components may have similar or different structure, functionalities and operation.

Device 40 typically is or includes an autonomous swallowable capsule, but may have other shapes, and need not be swallowable or autonomous. In one embodiment, device 40 includes an in-vivo camera, e.g., imager 46, which may capture and transmit images of the GI tract while the capsule passes through the GI lumen. Other lumens may be imaged. It is noted that in some embodiments, instead of imager 46 and/or in addition to it, other types of sensors may be used and/or may capture data, for example, a temperature sensor, a pH sensor, a pressure sensor, etc.

In one embodiment, imager 46 in device 40 may be connected to transmitter 41 also located in device 40. Transmitter 41 may transmit images to image device 12, which may send and/or transmit and/or upload and/or download the data to data processor 14 and/or to storage unit 19. Transmitter 41 may also include control capability, although control capability may be included in a separate component. Transmitter 41 may include any suitable transmitter able to transmit images and/or other data (e.g., control data) to a receiving device. For example, transmitter 41 may include an ultra low power Radio Frequency (RF) transmitter with high bandwidth input, possibly provided in Chip Scale Package (CSP). Transmitter 41 may transmit via antenna 48.

In some embodiments, transmitter 41 may include, for example, a transmitter-receiver or a transceiver, to allow transmitter 41 to receive a transmission. Additionally or alternatively, a separate or integrated receiver (not shown) or transceiver (not shown) may be used within device 40, instead of transmitter 41 or in addition to it, to allow device 40 to receive a transmission. In one embodiment, device 40 and/or transmitter 41 may, for example, receive a transmission and/or data and/or signal which may include commands to device 40. Such commands may include, for example, a command to turn on or turn off device 40 or any of its components, a command instructing device 40 to release a material, e.g., a drug, to its environment, a command instructing device 40 to collect and/or accumulate a material from its environment, a command to perform or to avoid performing an operation which device 40 and/or any of its components are able to perform, or any other suitable command. In some embodiments, the commands may be transmitted to device 40, for example, using a pre-defined channel and/or control channel. In one embodiment, the control channel may be separate from the data channel used to send data from transmitter 41 to receiver 12. In some embodiments, the commands may be sent to device 40 and/or to transmitter 41 using receiver 12, for example, implemented using a transmitter-receiver and/or transceiver, or using a separate and/or integrated transmitter (not shown) or transceiver (not shown) in the imaging system of FIG. 1.

Power source 45 may include one or more batteries. For example, power source 45 may include silver oxide batteries, lithium batteries, other suitable electrochemical cells having a high energy density, or the like. Other power sources may be used. For example, instead of internal power source 45 or in addition to it, an external power source may be used to transmit power to device 40.

Data processor 14 may analyze data received, such as image data, and may be in communication with storage unit 19, transferring data, such as frame data, to and from storage unit 19. Data processor 14 may also provide the analyzed data to image monitor 18 and/or position monitor 16, where a user may view the data. In one embodiment, for example, image monitor 18 may present an image of the GI lumen, and position monitor 16 may present the position in the GI tract at which the image was taken. In one embodiment, data processor 14 may be configured for real time processing and/or for post processing to be performed and/or viewed at a later time. Other monitoring and receiving systems may be used in accordance with embodiments of the invention.

In some embodiments, in addition to revealing pathological conditions of the GI tract, the system may provide information about the location of these pathologies. Suitable tracking devices and methods are described in embodiments of the above-mentioned U.S. Pat. No. 5,604,531 and/or U.S. patent application Publication No. US-2002-0173718-A1, filed May 20, 2002, titled "Array System and Method for Locating an In-Vivo Signal Source", assigned to the assignee of the present invention, and fully incorporated herein by reference.

It is noted that in embodiments of the invention, other location and/or orientation detection methods may be used. In one embodiment, the orientation information may include three Euler angles or quaternion parameters; other orientation information may be used. In one embodiment, location and/or orientation information may be determined by, for example, including two or more transmitting antennas in device 40, each with a different wavelength, and/or by detecting the location and/or orientation using a magnetic method. In some embodiments, methods such as those using ultrasound transceivers or monitors that include, for example, three magnetic coils that receive and transmit positional signals relative to an external constant magnetic field may be used. For example, device 40 may include an optional tracking and/or movement sensor 43.

In one embodiment, localization mechanism may be used; for example, a system using transmission from three or more stations. In one embodiment, if a phase and a frequency are used which are sufficiently high (e.g., 300 Megahertz), a resolution of 1 millimeter may be possible. Other types of localization mechanism may be used in accordance with embodiments of the invention. For example, an array of antennas or sensors may be placed on or close to the abdomen to enable tracking of device 40. Of course, other components or sets of components may be used in accordance with embodiments of the invention.

Optionally, device 40 may include a processing unit 47, for example, to process signals generated by imager 46. Processing unit 47 need not be a separate component; for example, processing unit 47 may be integral to imager 46 or transmitter 41, and may not be needed.

Optionally, device 40 may include one or more illumination sources 42, for example one or more "white LEDs" or any other suitable light source, for illuminating the body lumen.

In some embodiments, illumination sources 42 may provide, for example, ultra-violet light, infra-red light, or any other desired light or spectral range. In one embodiment, illumination sources 42 may include a laser source and/or may provide one or more laser beams.

In some embodiments, an optional optical system 50, including, for example, one or more optical elements (not shown), such as one or more lenses or composite lens assemblies (not shown), one or more suitable optical filters (not shown), or any other suitable mirror and/or lens and/or optical elements (not shown), may aid in focusing reflected light onto the imager 46 and/or performing other light processing.

Typically, device 40 transmits image information in discrete portions. Each portion typically corresponds to an image or frame. Other transmission methods are possible. For example, device 40 may capture an image once every half second, and, after capturing such an image, transmit the image to device 12. Other constant and/or variable capture rates and/or transmission rates may be used.

Typically, the image data recorded and transmitted is digital color image data, although in alternate embodiments other image formats (e.g., black and white image data) may be used. In one embodiment, each frame of image data includes 256 rows of 256 pixels each, each pixel including data for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by, for example, a one byte (i.e., 0-255) brightness value. Other data formats may be used.

Figure 2:
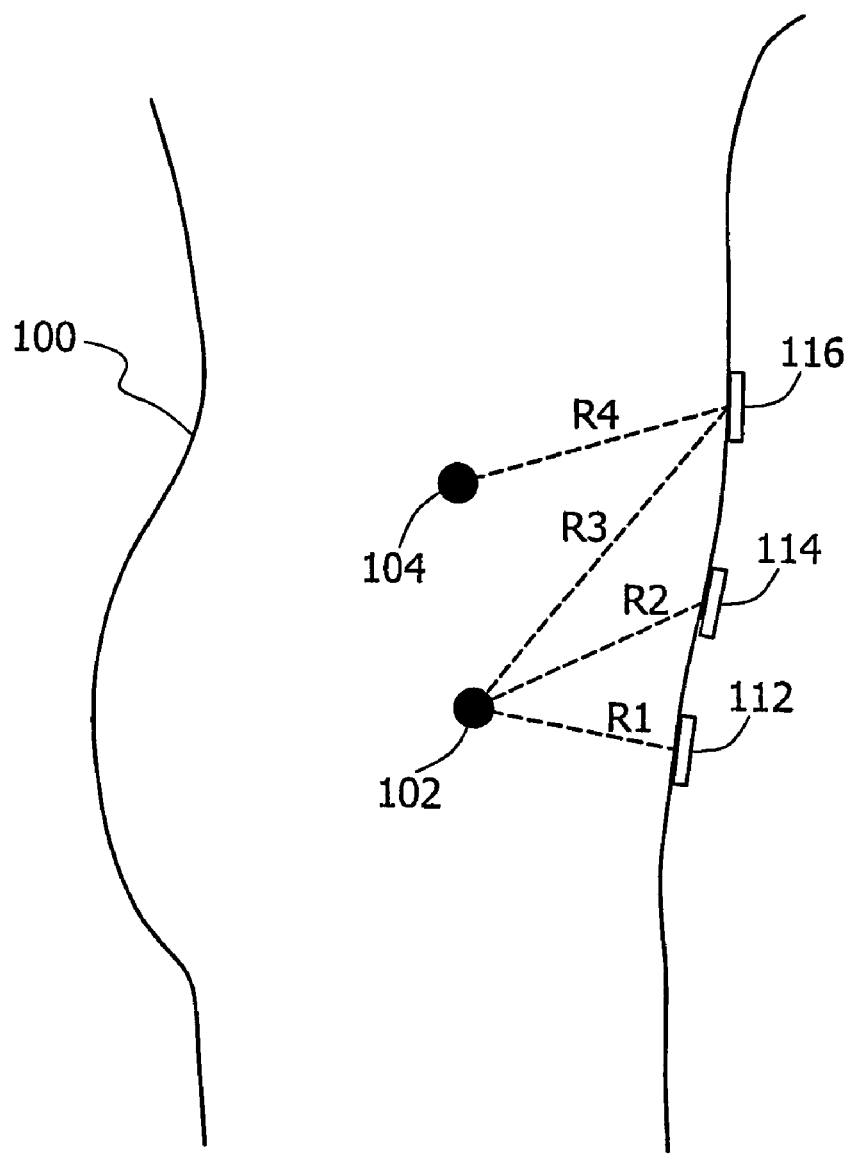
FIG. 2 is a schematic illustration ion of a body fitted with a set of antennas according to an embodiment of the present invention.

FIG. 2 schematically illustrates a side view of a body 100 fitted with three antennas 112, 114 and 116 according to an embodiment of the present invention. Other numbers of antennas may be used. Due to high attenuation of bodily tissues a condition may exist that enables device 40 location 102 to be received by antenna 112 (distance R1), and also register at the edge of reception level of antenna 114 (distance R2, when given R3>R2), but will not be received by antenna 116 (R3, when given R3>R2). When the capsule (not shown) moves to a new location 104, the best reception is by antenna 116 (distance R4) while the other antennas (112 and 114) may have a low reception level, or may be out of range.

According to embodiments of the present invention in order to ensure a stable reception a plurality of antennas may be used (e.g. an antenna array). It should be readily apparent that the more antennas in an antenna array, the better the coverage of the body and the better localization of the capsule. In some embodiments as few as three or four antennas properly positioned are sufficient to adequately locate the capsule during its transit inside the body.

Figure 3A:
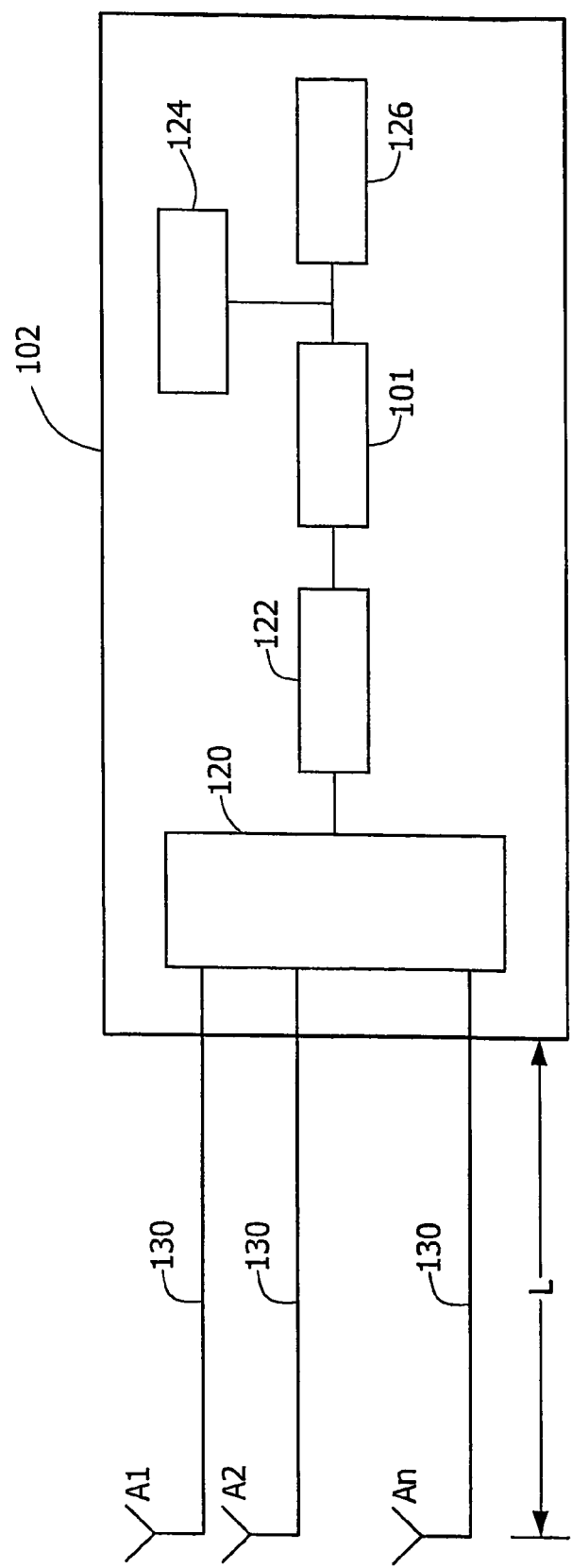
FIG. 3A is a schematic illustration of a device for receiving.

FIG. 3a is a schematic illustration of a recorder 102. Recorder 102 may include, for example, a receiver 101, a preamplifier 122, a processing unit 124 and a memory unit 126. Antennas A1-An, located at distance L from recorder 102 are connected to the recorder 102 by a plurality of cables 130. Cables 130 may attenuate signals received from the antennas A1-An, while not attenuating most of the noise components. Therefore the overall noise figure of receiver 101 is relatively lower in this case in comparison to cases where a direct attachment between the antennas An and the recorder is employed (e.g. L=0).

Figure 3B:
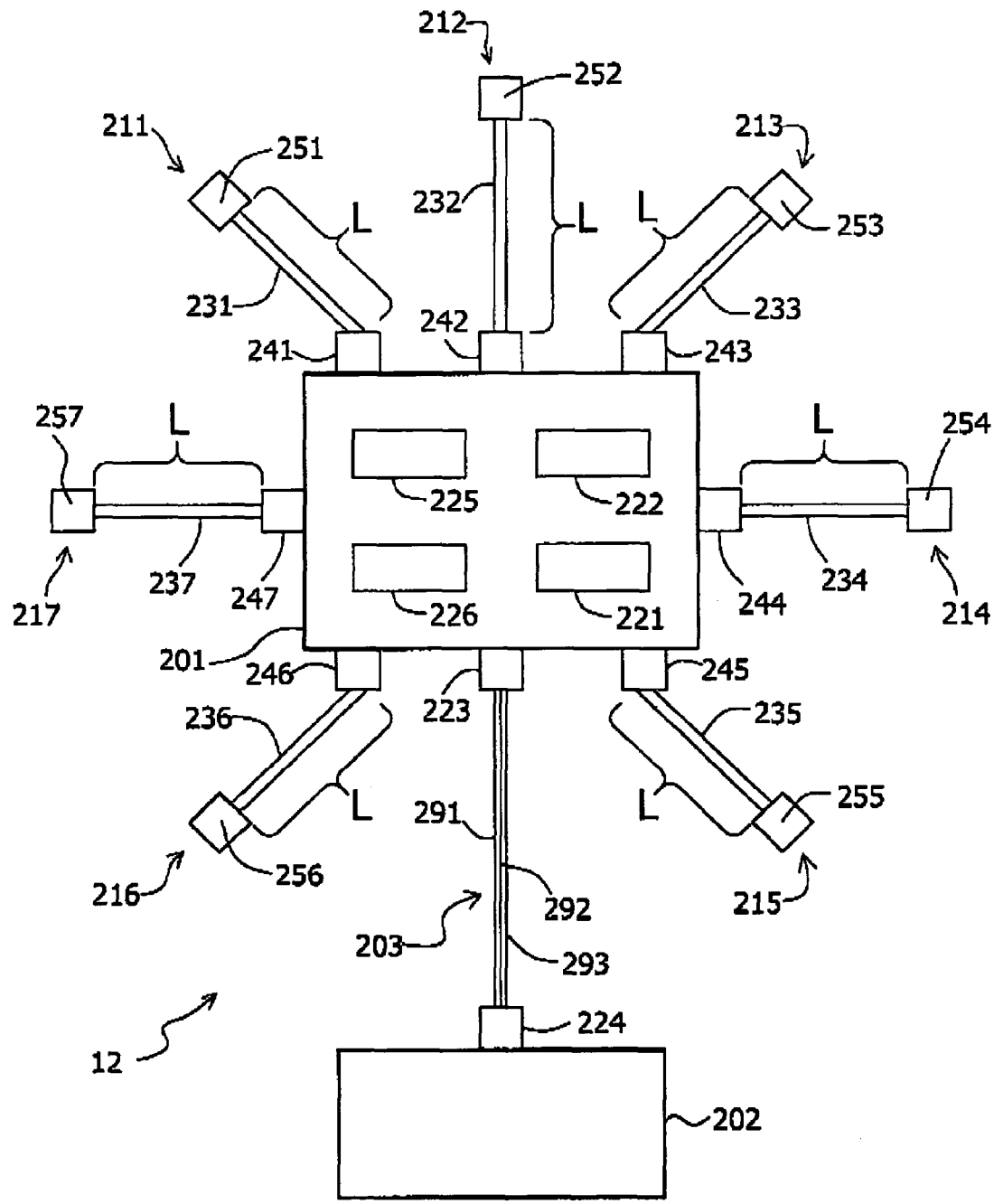
FIG. 3B is a schematic illustration of a device in accordance with an embodiment of the present invention.

FIG. 3b is a schematic illustration of a device 12 in accordance with an embodiment of the invention. Device 12 may include, for example, a receiver 201, a recorder 202, and optionally a connecting cable 203 to connect receiver 201 and recorder 202. In some embodiments, device 12 may be used in conjunction with the system of FIG. 1.

In some embodiments, receiver 201 may include one or more sensors and/or antennas In one embodiment, as indicated in FIG. 3b, receiver 201 may include seven antennas 211, 212, 213, 214, 215, 216 and 217. Of course, another number of antennas and/or sensors may be used in accordance with embodiments of the invention. Additionally or alternatively, in some embodiments, antennas 211 to 217 may include antennas and/or sensors of one type and/or of various types and properties.

Antennas 211 to 217 may include, for example, Radio Frequency (RF) antennas, which may include dipole antennas and/or any suitable units to receive a signal and/or a transmission. In some embodiments, antennas 211 to 217 may include, for example, a suitable transducer and/or other unit to receive and/or convert RF fields into electric current, or a suitable unit to receive and/or convert a signal, energy and/or data from one form to another form. Furthermore, in some embodiments, one or more of antennas 211 to 217 may include a sensor and/or a cable and/or a wire and/or a connector, as detailed herein.

Antennas 211 to 217 may be arranged, positioned, connected, placed and/or aligned to allow a desired reception of signals, for example, an optimal reception and/or a near-optimal reception and/or maximal signal strength and/or minimal error rate and/or minimal noise. For example, as illustrated schematically in FIG. 3b, antennas 211 to 217 may be arranged in a centralized pattern, in a circular pattern, to cover a desired area, etc. It is noted that some suitable patterns are shown in International Application WO 01/65995 and/or in U.S. Pat. No. 5,604,531. Of course, other shapes, areas, sizes and/or arrangements of antennas and/or sensors may be used in accordance with embodiments of the invention.

In some embodiments, antennas 211 to 217 may include, or may be connected to, components and/or sub-units as detailed herein. For example, antennas 211 to 217 may include cables 231 to 237 and sensors 251 to 257, respectively; antennas 211 to 217 may be connected to connectors 241 to 247, respectively. For purposes of simplicity, the following description may relate to an exemplary antenna 211; of course, identical or similar description and/or properties may apply to other antennas and/or sensors, for example, to antennas 212 to 217, which may have identical, similar and/or different properties. Hence, the description of antenna 211 may also relate to antennas 212 to 217; the description of cable 231 may also relate to cables 232 to 237; the description of connector 241 may also relate to connectors 242 to 247; and the description of sensor 251 may also relate to sensors 252 to 257.

In some embodiments, antenna 211 may include, for example, cable 231 and/or sensor 251. Cable 231 may include, for example, a coaxial cable and/or or any suitable cable, able to connect antenna 211 to receiver 201. Antenna 211 and/or cable 231 may be connected to receiver 201 using, for example, connector 241 of receiver 201. In some embodiments, cable 231 and/or antenna 211 may be detachable from connector 247 and/or from receiver 201.

Sensor 251 may include, for example, a wire and/or a coil of wire; in some embodiments, such wire may be, for example, linear, circular, square-shaped, triangular, rectangular, a flat sheet, a flat surface, or have another suitable form or shape. Optionally, sensor 251 may include, or may be held within, a suitable material, for example, an insulating material, e.g., cloth or plastic.

In some embodiments, sensors 251 to 257 may include, for example, Radio Frequency (RF) antennas, which may include dipole antennas and/or any suitable units to receive a signal and/or a transmission. In some embodiments, sensors 251 to 257 may include, for example, a suitable transducer and/or unit to receive and/or convert RF fields into electric current, or a suitable unit to receive and/or convert a signal, energy and/or data from one form to another form. Other types of sensors may be used in embodiments of the invention.

It is noted that in some embodiments, cable 231 and sensor 251 may be detachable from each other; in alternate embodiments, cable 231 and sensor 251 may be integrated, and/or may be implemented using one unit or several units.

In some embodiments, receiver 201 may include connectors 241 to 247. Other numbers of connectors may be used. Each of connectors 241 to 247 may include, for example, a coaxial plug and/or any suitable plug or connection, able to connect to antennas 211 to 217 and/or cables 231 to 237, respectively.

Optionally, in some embodiments, receiver 201 may include a switching unit 221. In some embodiments, switching unit 221 may be connected to the antennas and/or sensors of receiver 201, for example, to antennas 211 to 217. Optionally, such connection may allow an operator and/or a user and/or a patient and/or a physician to detach and/or disconnect one or more of antennas 211 to 217 from switching unit 221, if desired. Of course, detachable and/or non-detachable connections, for example, connectors 241 to 247, may be used to connect antennas 211 to 217 and switching unit 221.

In some embodiments, switching unit 221 may switch, combine, consolidate and/or route signals received by antennas 211 to 217 into one or more output signals transferred using, for example, connection 223.

It is noted that in some embodiments, switching unit 221 may be implemented as a separate component from recorder 202 and/or from antennas 211 to 217. Additionally or alternatively, in some embodiments, switching unit 221 may be connected electrically between antennas 211 to 217 and recorder 202. Furthermore, switching unit 221 may be electrically close, or significantly close (e.g close defined as electrical shorter distance), to antennas 211 to 217; and switching unit 221 may be closer, or significantly closer, to antennas 211 to 217 than recorder 202.

In some embodiments, switching unit 221 may consolidate and/or combine multiple signals for recording by recorder 202. For example, switching unit 221 may switch, route, combine and/or transfer, for example, to recorder 202, one or more signals out of a plurality of antenna signals received by switching unit 221. In some embodiments, switching unit 221 and/or receiver 201 may operate even if one or more of antennas 211 to 217 is not operational and/or is disconnected.

Additionally or alternatively, in some embodiments, switching unit 221 may include a selection unit 225. In some embodiments, selection unit 225 may include, for example, a manual and/or automatic switch to select one antenna and/or several antennas of antennas 211 to 217, such that only signals from the selected antenna or antennas are transferred through switching unit 221 to connection 223. In some embodiments, selection unit 225 may include or be associated with a detection unit 226 to detect and/or select a desired signal, for example, a strong signal, from signals received by antennas 211 to 217. In some embodiments, selection unit 225 may be operated manually and/or automatically and/or remotely, and may include any suitable combination of hardware and/or software. In one embodiment, selection unit 225 may include, for example, an RF selector or an RF switch. In some embodiments, switching unit 221 and/or receiver 201 may include an optional correlator unit (not shown) and/or an optional processor (not shown); such processor may, for example, select a signal and/or an antenna in accordance with a desired and/or suitable method or algorithm. For example, in one embodiment, the selection may be performed by sampling the signals received from each of antennas 211 to 217 for example in the beginning of each "frame" or transmission packet or data batch, and selecting the antenna with the strongest signal for receiving that "frame" or transmission packet or data batch. Other suitable selection methods and/or selection operations may be used in accordance with embodiments of the invention.

Optionally, in some embodiments, receiver 201 may include an amplifier 222. In some embodiments, amplifier 222 may be or may include a pre-amplifier. Amplifier 222 may, for example, amplify a signal or signals received by antennas 211 to 217, and/or may amplify a signal or signals transferred by switching unit 221. In some embodiments, amplifier 222 may be close, or significantly close, to antennas 211 to 217 and/or to the user's body. Such placement may be achieved, for example, by positioning amplifier 222 and/or receiver 201 in proximity (defined as short absolute distance) to antennas 211 to 217, and/or from using a suitable centralized pattern of antennas 211 to 217 which enables such close proximity of amplifier 222 to antennas 211 to 217 and/or to the user's body. Such proximity may allow, for example, better and/or significantly better signal amplification by amplifier 222, since a signal may travel a short or a relatively shorter distance from the antenna and/or sensor until it reaches amplifier 222 for amplification. Using some embodiments of the invention, better signal amplification may be achieved and/or signal degradation may be reduced or eliminated.

It is noted that in one embodiment, switching unit 221 and/or selection unit 225 and/or detection unit 226 and/or amplifier 222 may be implemented as separate units, as combined units, or as integrated units, and may include any suitable combination of hardware and/or software. Furthermore, some or all of these units may be combined within one chip, processor, circuit, controller and/or physical unit. Additionally or alternatively, the functionalities of switching unit 221 and/or selection unit 225 and/or detection unit 226 and/or amplifier 222 may be achieved using a plurality of separate chips, processors, circuits, controllers and/or physical units.

In one embodiment, it may be advantageous that selection unit 225 and/or switching unit 225 be in proximity to antennas 211 to 217, and/or in higher proximity to antennas 211 to 217 than recorder 202 or other units (e.g., L=0). This may allow, for example, more convenience in operation and/or use of device 12, since cables 231 to 237 may be shorter, lighter and/or less tangled. Additionally or alternatively, this may improve the performance of receiver 201 and/or its noise figure, for example, since amplifier 222 is in proximity to antennas 211 to 217 and therefore signals received by antennas 211 to 217 travel less distance before being amplified or pre-amplified by amplifier 222.

In some embodiments, a signal or signals received by antennas 211 to 217 may be switched and/or routed using switching unit 221, may be selected using selection unit 225, and/or may be amplified or pre-amplified using amplifier 222. Furthermore, in some embodiments, such signal or signals may be transferred and/or transmitted to another unit; such transmissions may be performed, for example, using a wired connection, for example, using cable 203 and connection 223, and/or using a wireless connection.

Cable 203 may be used to connect receiver 201 to recorder 202. In one embodiment, cable 203 may include, for example, one or more coaxial cables, and may be connected between connection 223 in receiver 201 and connection 224 in recorder 202. Cable 203 may be detachable from connection 223 and/or from connection 224. Connection 223 may include a coaxial connection, and/or connection 224 may include a coaxial connection.

In some embodiments, cable 203 may include one or more Bayonet Neil-Concelman/British Naval Connector (BNC) cables, and connectors 223 and 224 may each include a BNC plug and/or connector. Similarly, cables 231 to 237 may each include a BNC cable, and connectors 241 to 247 may each include a BNC plug and/or connector. Cables, connectors and/or plugs other than coaxial type and/or BNC type may be used in accordance with embodiments of the invention, and they may be of one type or of various types.

In one embodiment, cable 203 may include three cables: cable 291, which may transfer power and/or energy from receiver 201 to recorder 202 and/or vice versa; cable 292, which may transfer RF signals from receiver 201 to recorder 202 and/or vice versa; and cable 293, which may transfer control data, for example, for selecting an antenna from antennas 211 to 217 which signal to receive. Other numbers of cables may be used. In some embodiments, cable 203 may incorporate cables 291, 292 and 203 within one physical cable, and such that cable 203 connects to a single connector 223 and to a single connector 224. Other number of cables may be used within cable 203 and/or in addition to cable 203, and such cables may perform other suitable functionalities and/or may transfer other suitable types of data in accordance with embodiments of the invention.

Recorder 202 may include a unit to store signals, data and/or transmissions received by receiver 201 and transferred to recorder 202. It is noted that recorder 202 and/or receiver 201 may include an optional power source (not shown), for example, a battery, to provide energy for the operation of recorder 202 and/or receiver 201.

In some embodiments, receiver 201 may be a part of a wearable garment and/or clothing article, for example, a vest or a shirt. Additionally or alternatively, receiver 201, recorder 202 and cable 203 may be implemented using one or more integrated units.

It is noted that using device 12 to receive and/or record signals and/or data may allow several benefits. For example, in some embodiments, device 12 may be implemented as or within a wearable garment, allowing convenient usage, ease of use, comfortable use, comfortable body temperature, attractive appearance and/or esthetic layout. Such convenience would be appreciated, for example, by patients and/or physicians, in contrast, for example, to bonding and/or gluing antennas to a patient's bare skin.

Additionally or alternatively, some embodiments of the invention may allow a modular usage, a flexible usage and/or a modifiable usage of device 12. For example, in some embodiments, device 12 may be implemented using receiver 201, recorder 202 and cable 203, such that each one of them may be replaced and/or modified separately, if desired. In some embodiment, a modification may be performed to receiver 201, for example, modifying the type and/or number and/or arrangement of antennas and/or sensors, without requiring a modification of recorder 202.

Additionally or alternatively, in some embodiments, for example, each of receiver 201, recorder 202 and/or cable 203 may be replaced and/or fixed separately due to breakage or wear and tear, may be separately subject to maintenance and/or preventive maintenance, may be separately available for examination and/or debugging, may be separately replaced and/or modified to achieve various desired functionalities, and/or may include a separate serial number which may be used for various tracking and/or inventory purposes.

In some embodiments, receiver 201 and/or recorder 202 may automatically adjust their operation to the number and/or types of antennas and/or sensors used in device 12. Such automatic adjustment may be achieved, for example, by using serial numbers to indicate properties of receiver 201 and/or recorder 202, such that one unit may automatically identify the other unit and may adjust its functionality accordingly. In one embodiment, the implementation of device 12 using separate units for receiver 201 and recorder 202 may, for example, "insulate" recorder 202 from direct connection with a plurality of sensors and/or antennas, e.g., antennas 211 to 217, thus eliminating and/or reducing the need of recorder 202 to adjust its operation to changeable number and/or type of sensors and/or antennas.

In some embodiments, recorder 202 may detect the presence or the absence of receiver 201, and may respond accordingly. For example, recorder 202 may detect that receiver 201 is connected to recorder 201, and/or that receiver 201 is operational and/or receiving signals; recorder 201 may thus respond, for example, by recording signals received from receiver 201. Alternatively, recorder 201 may, for example, detect that receiver 201 is not connected to recorder 202, and/or that receiver 201 is not operational and/or not receiving signals; recorder 201 may thus respond, for example, by not recording data, or by recording data indicating the above detection, or by pausing and/or stopping to record data.

Additionally or alternatively, in some embodiments, device 12 may allow an automatic identification of various types of sensors and/or arrays and/or receivers such as receiver 201. For example, in some embodiments, recorder 202 may be able to automatically identify the type and/or serial number of receiver 201, or vice versa, to achieve various functionalities and/or compatibility. Such automatic identification may be achieved, for example, using unique serial numbers which indicate and/or encapsulate information describing their properties.

In some embodiments, cable 203 may include a single cable, for example, a single coaxial cable, in contrast to a plurality of cables. In some embodiments, using a single cable 203 may allow, for example, using a simpler connector 223, using a simpler connector 224, using a simpler coaxial connector 223, using a simple coaxial connector 224, using a cable 223 available from a larger selection of suitable cables, and/or using connector 223 and/or cable 224 available from a larger selection of suitable connectors.

In some embodiments, device 12 may be implemented using receiver 201, recorder 202 and cable 203, such that recorder 202 includes less or significantly less components and/or cables than a typical recorder unit. For example, recorder 202 may include a reduced number of connectors, such as connector 224 or several connectors similar to connector 224, in contrast to a conventional recorder which may include numerous connectors connected to numerous cables, sensors and/or antennas.

Additionally or alternatively, in some embodiments, device 12 may have better sensitivity and/or reception capability. For example, in some embodiments, antennas 211 to 217 may be shaped as lines or straight lines, e.g. in a pattern and/or shape similar to FIG. 2, which may allow signals to travel a short or a relatively short route, for example, until they are amplified by amplifier 222 and/or recorded by recorder 202. In some embodiments, amplifier 222 may be close or relatively close to antennas 211 to 217, allowing better and/or stronger amplification of signals, and/or allowing amplification of signals before transferring them to recorder 202.

Additionally or alternatively, in some embodiments, device 12 may optionally include one or more self-test units (not shown). For example, in some embodiments, a self-test unit may be included in receiver 201 and/or recorder 202. Such self-test unit may allow, for example real-time and/or on-line testing of receiver 201, of recorder 202, of antennas 211 to 217, of the sensitivity and/or reception of antennas 211 to 217, etc.

In some embodiments, device 12 may allow a better positioning and/or stronger positioning and/or easier positioning of recorder 202. For example, recorder 202 may include a reduced number of connectors, and/or may be connected to a reduced number of cables, thus allowing recorder 202 to be more easily positioned and/or to be more stable in its place.

In some embodiments, one or more of sensors 251 to 257 and/or one or more of antennas 211 to 217 may be attached to a user's skin and/or body by adhesion, either directly and/or indirectly, for example, using an adhesive sleeve and/or cloth.

It is noted that in some embodiments, it may be advantageous that device 12 may include a plurality of antennas, for example, 211 to 217, to cover substantially the entire body areas in which device 40 may travel. A plurality of antennas, and/or their positioning and alignment, may allow device 12 to receive transmissions sent by device 40 even though some body areas and/or tissues may create attenuation.

Figure 3C:
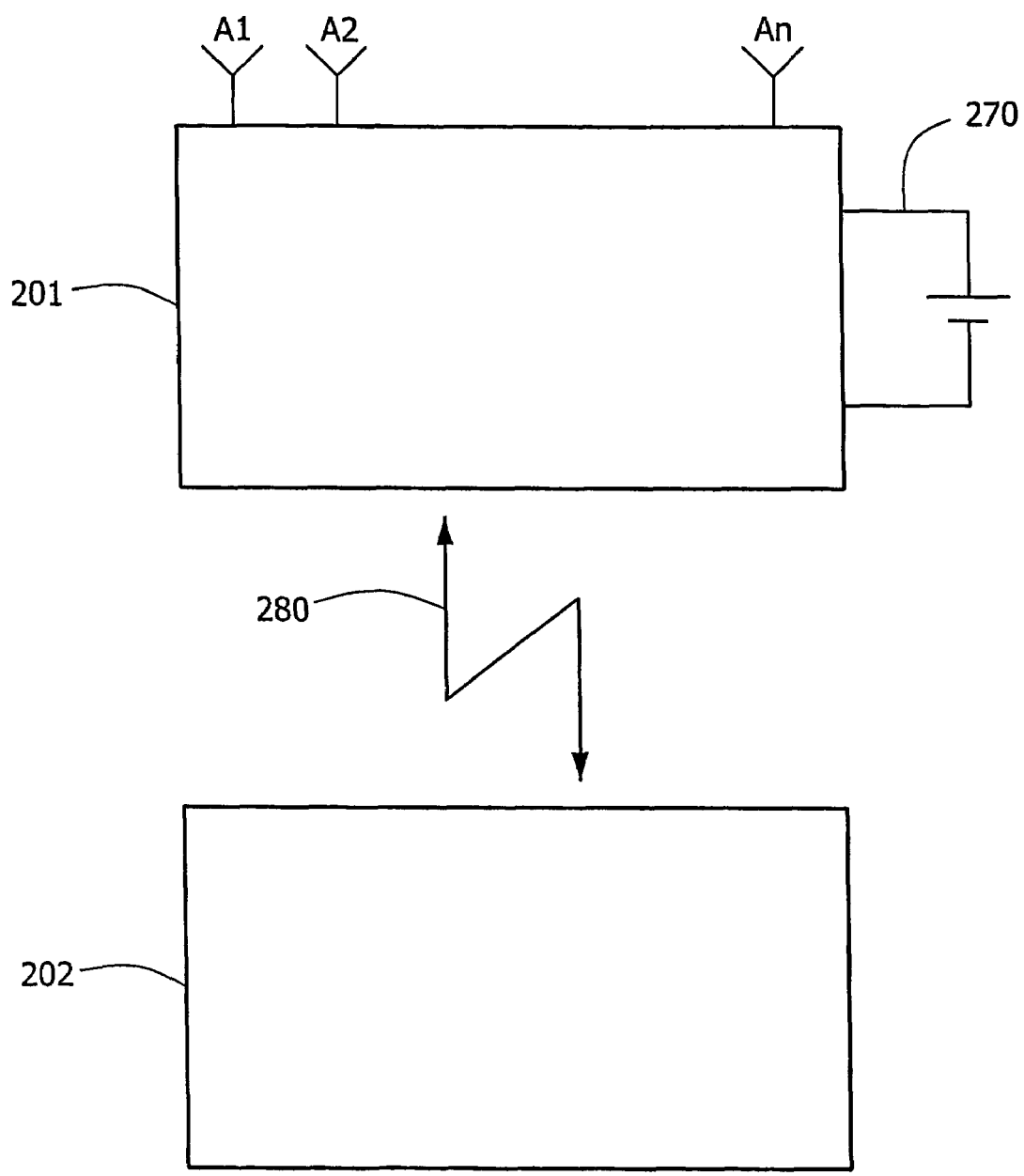
FIG. 3C is a schematic illustration of a device in accordance with another embodiment of the present invention.

FIG. 3c schematically illustrates a receiver 201 and a recorder 202 according to another embodiment of the present invention. Recorder 202 may include a power source 270, for example a battery, and may be in electrical communication through wireless channels 280 to receiver 201.

Figure 4:
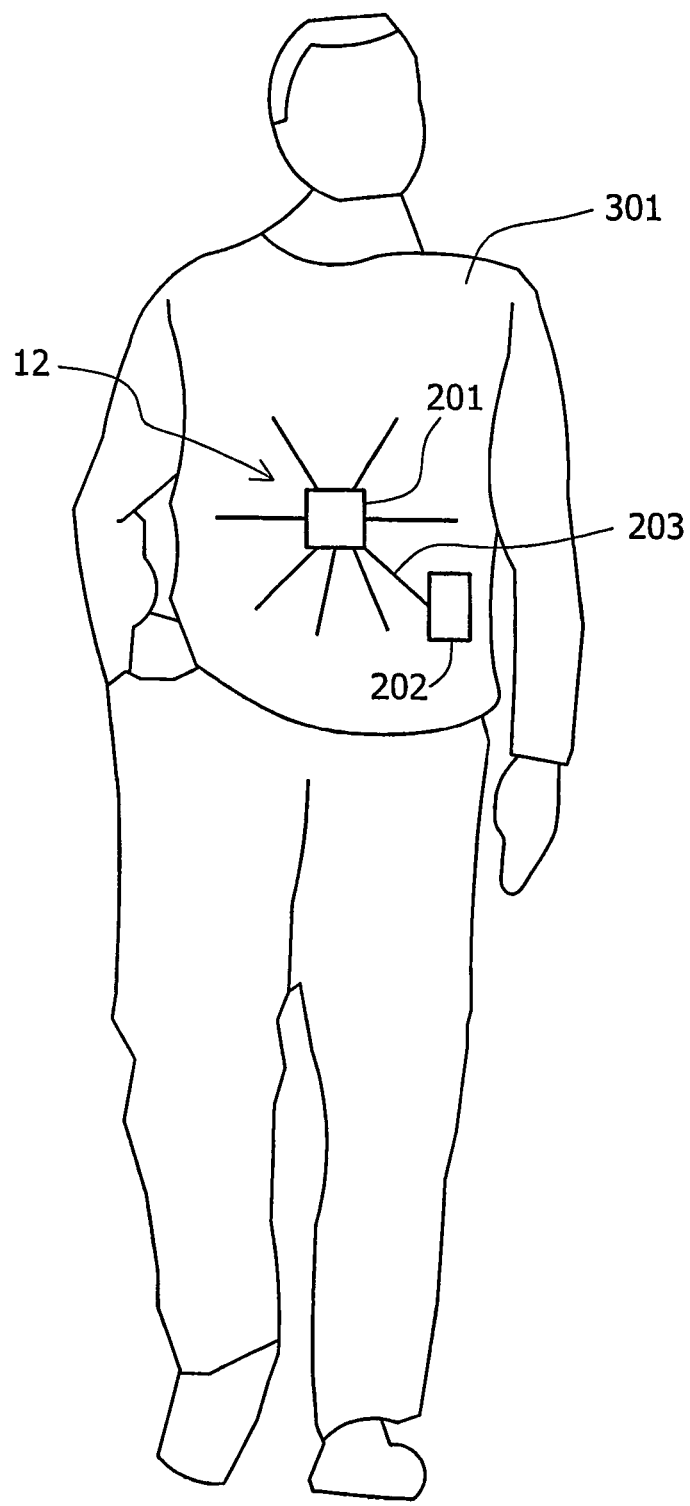
FIG. 4 is a schematic illustration of a wearable article incorporating a device in accordance with an embodiment of the invention.

FIG. 4 is a schematic illustration of a wearable article 301 incorporating device 12 in accordance with an embodiment of the invention. In some embodiments, device 12 may be implemented and/or incorporated as, or be a part of, article 301. In some embodiments, article 301 may include, for example, a vest, shirt, long-sleeve shirt, short-sleeve shirt, T-shirt, sleeveless shirt, sleeve-less garment, pullover, sweat-shirt, training-shirt, bra, sports-bra, under-garment, jacket, blouse, top, gown, dress, robe, coat, belt, plurality of belts, horizontal and/or vertical and/or diagonal belts, or other article of clothing. In some embodiments, article 301 may be provided in various sizes to fit various body dimensions of different users, or, alternatively, article 301 may be provided in standard and/or average "one size fits all" dimensions to accommodate a wide variety of person sizes. In some embodiments, article 301 may be washable and/or cleanable.

In some embodiments, article 301 may include device 12. In alternate embodiments, article 301 may include receiver 201 and/or recorder 202 and/or recorder 203, and/or one or more components of these units. Article 301 may include various design features and/or functionality features common in wearable garments, for example, article 301 may include one or more buttons, zippers, Velcro connectors, laces, pockets, etc.

In some embodiments, article 301 incorporating device 12 may be, for example, put on by a patient, such that device 12 may be positioned in proximity or in relative proximity to a desired body area to allow better and/or stronger capacity to receive and/or amplify and/or record signals and/or transmissions. In some embodiments, for example, article 301 may be placed in proximity to a patient's stomach and/or back and/or GI tract. Of course, article 301 may be worn and/or placed in proximity to other body areas, as desired to achieve various benefits and/or functionalities. It is noted that using article 301 in accordance with embodiments of the invention may obviate and/or reduce a need to glue, attach and/or bond sensors and/or cables to a patient's body.

In some embodiments, article 301 may be washable and/or re-usable by various users. In some embodiments, article 301 may incorporate device 12 and/or receiver 201 and/or recorder 202 and/or cable 203, such that one or more of these units may be detachable from article 301, to allow removal and/or replacement of such units.

In some embodiments, device 12 and/or receiver 201 and/or recorder 202 may be implemented and/or incorporated as a bed, mattress, blanket, table, carpet, board, flat board, substantially flat pane, etc. Such implementations and embodiments may, for example, allow a patient to lie down over such device 12 to receiver and/or record signals.

It is noted that other various benefits may be achieved using embodiments of the invention.

Figure 5:
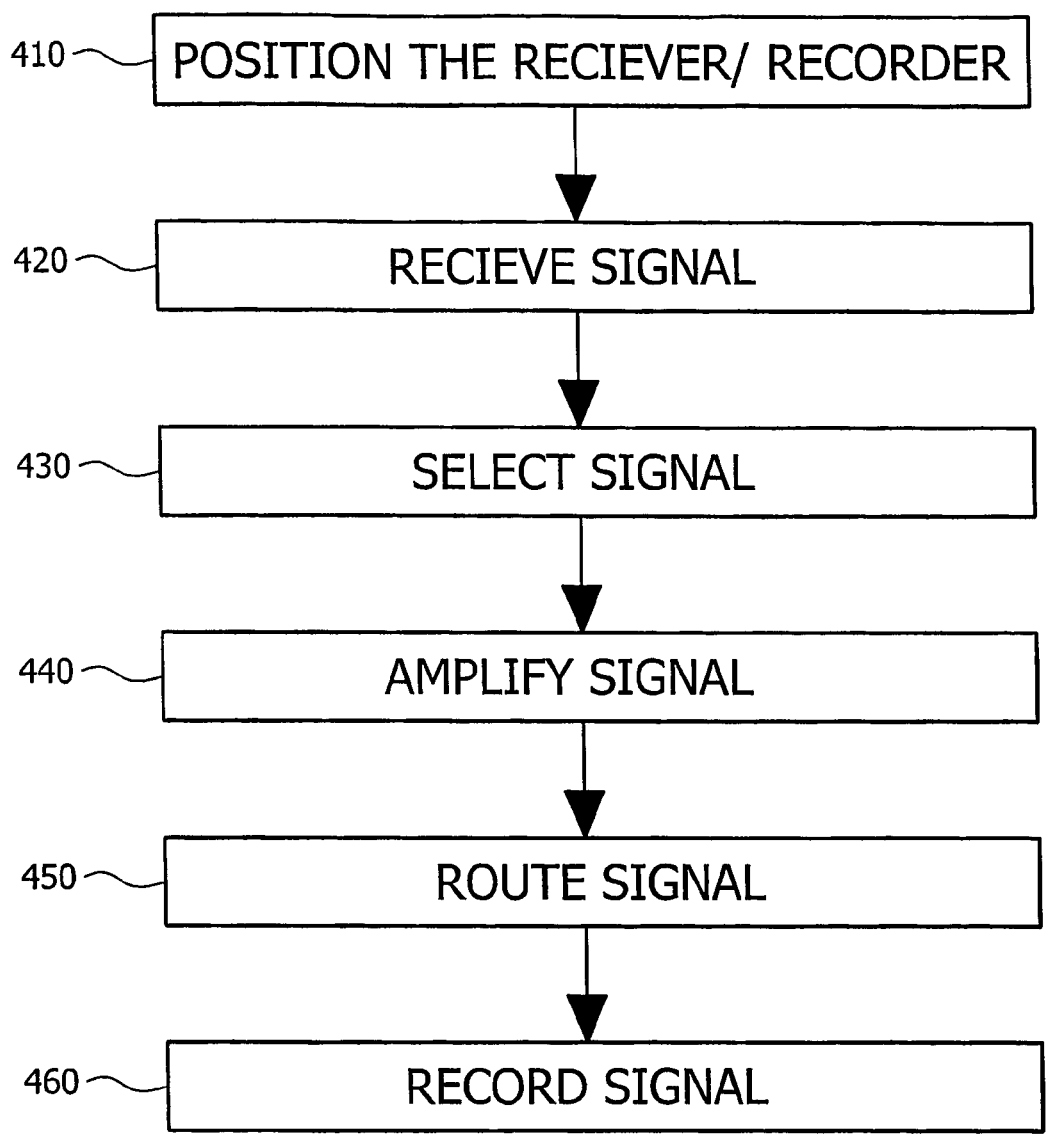
FIG. 5 is a flow chart diagram of a method of receiving and/or recording transmissions in accordance with an embodiment of the invention.

FIG. 5 is a flow chart diagram of a method of receiving and/or recording transmissions in accordance with an embodiment of the invention. As indicated at block 410, device 12 may be placed and/or positioned, for example, in proximity to a patient's body.

As indicated at block 420, signals and/or transmissions may be received by receiver 201.

Optionally, as indicated at block 430, in some embodiments, one or more sensors, for example, one or more of antennas 211 to 217, may be selected for further routing and/or amplification and/or recording. In some embodiments, the selection may be performed manually and/or automatically. In some embodiments, the selection may be based on, for example, signal strength, relative signal strength in comparison to other signals' strength, signal strength in comparison to a pre-defined threshold, or other desirable criteria.

Optionally, as indicated at block 440, the signal and/or signals received and/or selected may be amplified. Such amplification may include, for example, pre-amplification.

As indicated at block 450, the signal and/or signals received and/or selected and/or amplified may be routed, for example, to recorder 202 using cable 203.

As indicated at block 460, the signal and/or signals may be recorded by recorder 202. In some embodiments, for example, signals, transmissions and/or data may be stored by recorder 202.

Other operations and/or series of operations may be used in accordance with embodiments of the invention.

While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

What is claimed is:

1. A method for adjusting operation of an in vivo sensing system, the method comprising:
   detecting the presence or absence of a receiver connected by cable to a recorder, the receiver receiving image signals from a plurality of antennas placed on a body;
   upon detecting the presence of the receiver:
      identifying the type of the receiver;
      automatically adjusting operation of the recorder according to the type of receiver identified;
      transferring data received by the receiver to the recorder; and
      storing in the recorder data transferred from the receiver; and
   upon detecting the absence of the receiver, automatically adjusting the operation of the recorder, wherein automatically adjusting the operation of the recorder comprises an operation selected from the group consisting of: not recording data, recording data indicating a receiver is not connected, and stopping to record data.

2. The method according to claim 1, wherein the plurality of antennas comprises a radio frequency antenna.

3. The method according to claim 1, wherein the receiver receives signals selected from a group consisting of: radio frequency signals, control data, and energy.

4. The method according to claim 1, wherein the receiver is to adjust its operation according to the number of the plurality of antennas.

5. The method according to claim 1, wherein the signals are pre-amplified prior to being transferred to the recorder.

6. The method according to claim 1, wherein the strongest signal from the plurality of antennas is selected for recording.

7. The method according to claim 1 wherein the plurality of antennas receive image signals from an in-vivo imaging capsule.

* * * * *